United States Patent [19]

Pearce

[11] Patent Number: Plant 7,196

[45] Date of Patent: Mar. 20, 1990

[54] ROSE PLANT PEAMIGHT

[75] Inventor: Collin Pearce, Kelly, England

[73] Assignee: Jackson & Perkins Company, Medford, Oreg.

[21] Appl. No.: 307,511

[22] Filed: Feb. 6, 1989

[51] Int. Cl.[4] ..... A01H 5/00

[52] U.S. Cl. ..... Plt./5

[58] Field of Search ..... Plt. 5

*Primary Examiner*—Robert E. Bagwill

*Attorney, Agent, or Firm*—Majestic, Parsons, Siebert & Hsue

[57] ABSTRACT

A rose variety of the climbing class is provided that has pleasant coral pink to pink flowers and a light fragrance. It is a vigorous, climbing plant with leathery green foliage and is mildew resistant.

1 Drawing Sheet

SUMMARY OF THE INVENTION

The present invention relates to a new and distinct variety of rose plant of the climbing class, which was originated by me by crossing an unnamed variety with an unnamed variety.

The primary objective of this breeding was to produce a new rose variety of the climbing class with unique color of flower, good foliage and vigorous growth. This objective was substantially achieved, along with other desirable improvements, as evidenced by the following unique combination of characteristics which are outstanding in the new variety and which distinguish it from its parent as well as from all other varieties of which I am aware. For example, this new rose variety has:

1. Coral pink to pink flower color;
2. Long arching, climbing canes;
3. Moderate, pleasant fragrance;
4. Leathery green foliage; and
5. Resistance to powdery mildew.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "PEAMIGHT". Color terminology is in accordance with The Royal Horticultural Society Colour Chart except where an ordinary dictionary significant for the color is apparent.

Observations of the buds and flowers were made from specimens grown in a greenhouse environment in November at Somis, Calif.

Flower

The blooming habit is recurrent. The bud size is one and one-half inches when the petals start to unfurl. The bud form is pointed ovoid. The bud color when sepals first divide is near Orange-Red Group 35A. When half blown, the upper side of petals is near Red Group 39C. The lower side of petals is near Red Group 39C. The sepals have a color near Yellow-Green Group 147B. The outside surface texture of the sepals is smooth and glabrous. There are three normally appendaged sepals, and two unappendaged sepals with a hairy edge. The receptacle color is near Green Group 138B and has an apple shape, broad size and smooth surface. The peduncle is short in length and has a smooth surface. Peduncle color is light green and the peduncle is stiff and erect.

Bloom

Bloom size is medium with an average open size of three to three and one-half inches, borne singly and in rounded clusters. The stems are strong and long. The form when first open is high center, and towards the end of the bloom flattens with the outer petals curling back. Under normal conditions there are 20 to 25 petals. At the center of the flower, the upper side of the petals are near Red Group No. 37A and the reverse side of the petals at the flower center are near Red Group 37B. At the point of attachment at the base of petals, there is a crescent near Yellow Group 9C. The major color is near Red Group 37B. There are no variegations.

There is moderate fragrance. The petal texture is leathery. The petal shape is round and pointed and the form is flat, tips slightly recurved. The arrangement is imbricated with no petaloids in the center. The blooms drop off cleanly, and last both on the plant and as a cut flower for a long time.

Reproductive Parts

The anthers are of medium size, of yellow color and arranged regularly around the styles. The filaments are yellow, the pollen is gold yellow, the styles are white at the base, turning pink near the stigma, and the stigmas are white.

Plant

The plant is a vigorous growing climber.

Foliage

The foliage is large size and normal in quantity. New foliage is green with a purple-red underside and old foliage is near Green Group 139A. A normal mid-stem leaf has five and seven leaflets.

The leaflets have an oval pointed shape, are leathery in texture, and have a serrated edge. The serration is double and small. Petiole rachis is green, and petiole underside has prickles. Stipules are medium. The foliage is resistant to mildew under normal growing conditions at Somis, Calif.

Wood

New wood is light green with a smooth bark. Old wood is green with a smooth bark.

Prickles

There are a few to an ordinary number of prickles on the main canes from the base and a few prickles on the laterals from the main canes. The prickles are short and hooked downward and are red colored when young.

There are no small prickles on the main stalks or on the laterals.

Parentage

The seed parent was of an unnamed variety. The pollen parent was of unnamed variety.

Classification

Botanical is rosa hybrid. Commercial is climbing.

I claim:

1. A new and distinct variety of rose plant of the climbing class substantially as herein shown and described, characterized particularly as to novelty by its active climbing habit, coral pink to pink flower color, light fragrance, leathery foliage, resistance to mildew and overall plant vigor.

* * * * *

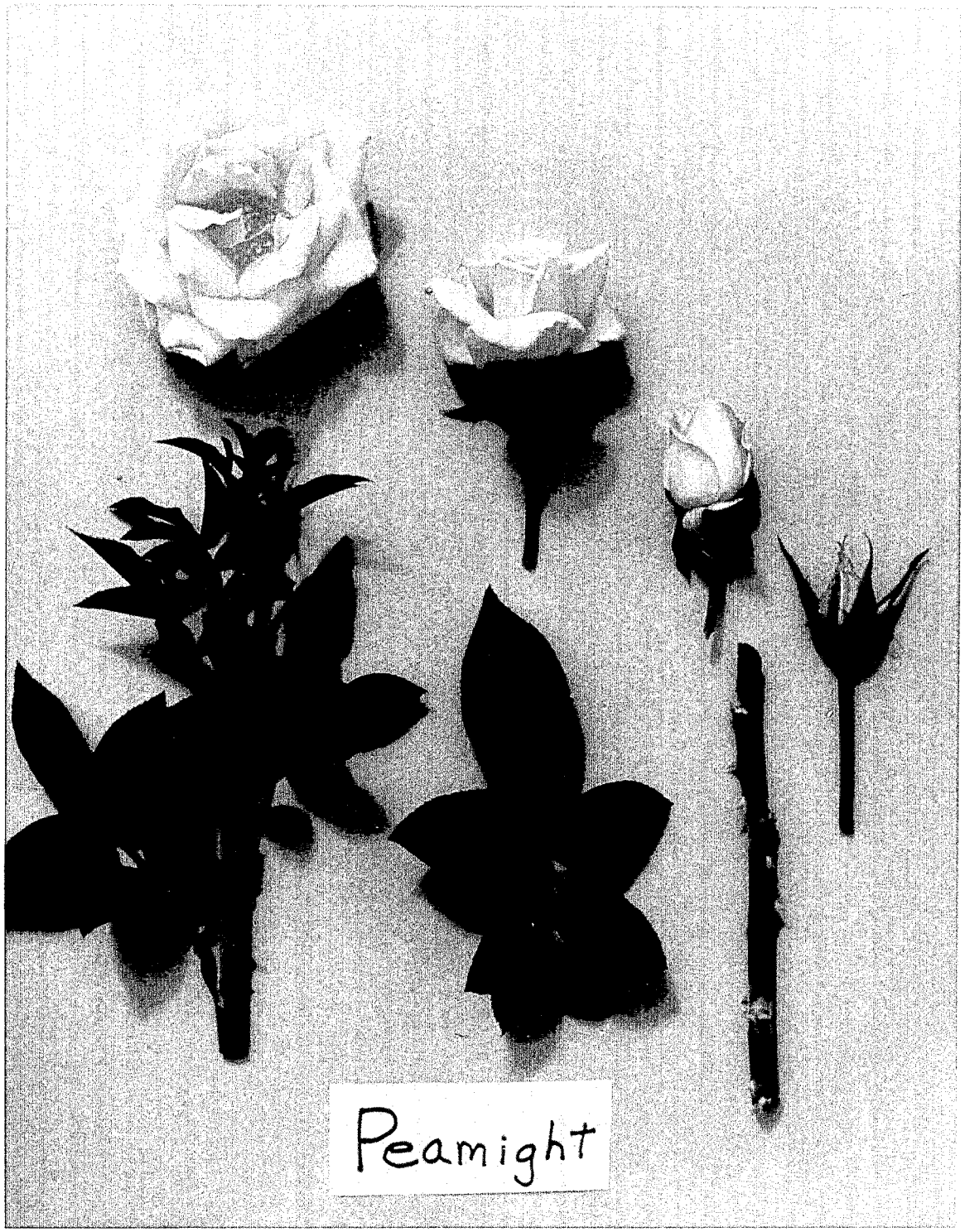
Peamight